United States Patent [19]

Krause

[11] Patent Number: 4,859,703

[45] Date of Patent: Aug. 22, 1989

[54] LIPID REGULATING COMPOSITIONS

[75] Inventor: Brian R. Krause, Ann Arbor, Mich.

[73] Assignee: Warner-Lambert Company, Morris Plains, N.J.

[21] Appl. No.: 61,641

[22] Filed: Jun. 15, 1987

[51] Int. Cl.$^4$ .................. A61K 31/235; A61K 31/24; A61K 31/195; A61K 31/16
[52] U.S. Cl. ................................ 514/543; 514/537; 514/563; 514/571; 514/627; 514/824; 260/DIG. 47
[58] Field of Search .............. 514/563, 571, 532, 533, 514/627, 543

[56] References Cited

U.S. PATENT DOCUMENTS

| | | | |
|---|---|---|---|
| 3,262,850 | 7/1966 | Jones | 167/65 |
| 3,674,836 | 7/1972 | Creger | 260/473 |
| 3,781,327 | 12/1973 | Teach | 260/471 |
| 3,846,541 | 11/1984 | Lachampt | 424/170 |
| 3,907,792 | 9/1975 | Mieville | 260/247.2 B |
| 4,751,026 | 6/1988 | Hoefle et al. | 260/404 |

FOREIGN PATENT DOCUMENTS 0010299  5/1980  European Pat. Off. .

OTHER PUBLICATIONS

M. S. Brown and J. L. Goldstein, *New England Journal of Medicine*, 305 (9): 515-517 (1981).
Saku et al., *J. Clin. Invest.*, 75: 1702-1712 (1985).
Ottmar Leiss et al., *Metabolism*, 34 (1): 74-82 (1985).
S. M. Grundy et al., *J. Lipid Res.*, 13: 531-551 (1972).
D. Pertsemlidis et al., *Gastroenterology*, 66: 565-573 (1974).
K. von Bergmann et al., *Europ. J. Clin. Invest.*, 14: 150-154 (1984).

*Primary Examiner*—Douglas W. Robinson
*Assistant Examiner*—Raymond J. Henley, III
*Attorney, Agent, or Firm*—Ronald A. Daignault

[57] ABSTRACT

Single dose formulations containing a combination of a lipid regulating agent selected from gemfibrozil, clofibrate, bezafibrate, or fenofibrate and an ACAT inhibiting agent are effective pharmacological formulations for regulating blood serum lipid and cholesterol levels.

2 Claims, No Drawings

LIPID REGULATING COMPOSITIONS

BACKGROUND OF THE INVENTION

The present invention is related to pharmaceutical compositions and methods of treatment. More particularly it concerns pharmaceutical compositions comprising combinations of blood serum lipid and cholesterol regulating agents.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which are effective in lowering total serum cholesterol levels. However, it has since been discovered that the mechanism by which cholesterol is transported in the blood and deposited as plaques on vascular walls is quite complex. Current understanding of the problem differentiates between the different forms of lipoprotein cholesterol which circulate in the blood stream and it is now believed that effective approaches to the control of blood serum cholesterol involve more than merely reducing the levels of total serum cholesterol.

For example, it is now known that cholesterol is transported in the bloodstream in the form of complex particles consisting of a core of cholesteryl esters or triglycerides and an surface coat consisting primarily of phospholipids, free cholesterol, several types of protein termed apolipoproteins which can be recognized by specific receptors. For example, cholesterol is carried to the sites of removal such as cells of the arterial wall in the form of low density lipoprotein cholesterol (LDL cholesterol) and away from such sites by high density lipoproteins. The LDL in peripheral cells is recognized by LDL receptors (or modified LDL receptors) and the HDL may be recognized by HDL receptors. Therefore, traffic in both directions depends upon apolipoprotein interactions.

Following these discoveries, the search for therapeutic agents which control serum cholesterol has increasingly turned to finding compounds which are more selective in their action; that is, agents which are effective both in elevating the serum levels of HDL cholesterol and/or lowering the levels of LDL cholesterol, and in lowering serum triglycerides.

One approach to lowering total and LDL-cholesterol levels in blood serum has centered around the discovery of therapeutic agents which inhibit the enzyme 3-hydroxy-3-methylglutaryl coenzyme A reductase (HMG-CoA reductase). This enzyme is the rate-limiting step in the biosynthesis of cholesterol, and it is known that inhibitors of HMG-CoA reductase are effective in lowering the level of plasma cholesterol, especially LDL-cholesterol, in man (cf. M. S. Brown and J. L. Goldstein, *New England Journal of Medicine*, 305 (9): 515–517 (1981).

In an alternative approach to the control of serum lipoproteins and cholesterol, it has been found that 5-(2,5-dimethylphenoxy)-2,2-dimethylpentanoic acid (commonly known as gemfibrozil) acts to elevate plasma levels of HDL-cholesterol and to decrease plasma triglycerides. This pharmacological action is an effective method of treating a variety of primary and secondary dislipoproteinemias. (See Saku et al., *J. Clin. Invest.*, 75: 1702–1712 (1985)).

Agents which lower serum cholesterol levels also tend to raise the concentrations of cholesterol found in bile, since the conversion of cholesterol to bile acids is one mechanism by which the body eliminates cholesterol.

Gemfibrozil has been shown to be effective in increasing the amount of cholesterol excreted in to bile. (See Ottmar Leiss et al., Metabolism, 34 (1): 74–82 (1985).

Likewise the fibric acid derivatives such as clofibrate (i.e. 2-(4-chlorophenoxy)-2-methylpropanoic acid, ethyl ester), bezafibrate (i.e. 2-[4-[2-[(4-chlorobenzoyl)amino]ethyl]phenoxy]-2-methylpropanoic acid), and fenofibrate (i.e. 2-[4-(4-chlorobenzoyl)phenoxy]-2-methylpropanoic acid, 1-methylethyl ester) are effective in increasing the concentrations of biliary cholesterol. (See S. M. Grundy et al., *J. Lipid Res.*, 13: 531–551 (1972); D. Pertsemlidis et al., *Gastroenterology*, 66: 565–573 (1974); and K. von Bergmann et al., *Europ. J. Clin. Invest.*, 14: 150–154 (1984)).

Bile acid sequestering agents such as cholestipol and cholestyramine lower plasma cholesterol by sequestering bile acids in the intestinam lumen. The net result is the up-regulation of liver LDL receptors as occurs with HMG-CoA reductase inhibitors.

While each of the foregoing types of cholesterol-controlling agents are effective in moderating the levels of serum cholesterol and triglycerides, or increasing the concentrations of biliary cholesterol, they have little or no direct effect on controlling the initial adsorption of dietary cholesterol in the body through the intestinal wall or the reabsorption of cholesterol from the bile in the intestine.

In intestinal mucosal cells, dietary cholesterol is absorbed as free cholesterol which must be esterified by the action of the enzyme acyl-CoA:cholesterol acyltransferase (ACAT) before it can be packaged into the chylomicrons which are then released into the blood stream. Thus, therapeutic agents which effectively inhibit the action of ACAT prevent the intestinal absorption of dietary cholesterol or the reabsorption of cholesterol which has been previously released into the intestine through the biliary system.

Some attempts have been made to find effective combinations of therapeutic agents to control serum cholesterol and lipid levels. U.S. Pat. No. 3,846,541 discloses the coadministration of chlorophenoxy isobutyric acid and its esters with a bile acid sequestering agent. Such combinations result in some lowering of low-density and total cholesterol, but result in compensatory increases in cholesterol biosynthesis.

European Patent Application 0 010 299 discloses combinations of HMG-CoA reductase inhibitors and bile acid sequestrants which are effective in lowering LDL-cholesterol but have minimal effect on HDL-cholesterol.

SUMMARY OF THE INVENTION

The present invention provides a pharmaceutical composition comprising a first component selected from compounds having lipid regulating activity and effective in increasing biliary concentrations of cholesterol, selected from gemfibrozil, clofibrate, bezafibrate, and fenofibrate, and a second component selected from compounds having ACAT inhibitory activity having the structure

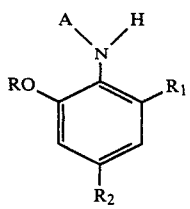

together with a pharmaceutically acceptable carrier.

The first and second components of the pharmaceutical composition are present in a weight ratio of respectively between 1:1 and 1:3.

In the compounds forming the second component described above, A is selected from

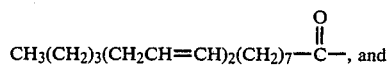

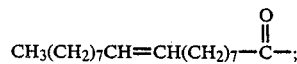

where $R_1$, and $R_2$ are independently selected from straight or branched alkyl of from one to four carbon atoms, straight or branched alkoxyl of from one to four carbon atoms, or halogen, and where R is straight or branched alkyl of from one to four carbon atoms.

DETAILED DESCRIPTION

The terms "alkyl" and "lower alkyl" as used throughout this specification and the appended claims mean a branched or unbranched hydrocarbon grouping derived from a saturated hydrocarbon of from one to four carbon atoms by removal of a single hydrogen atom. Examples of alkyl groups contemplated as falling within the scope of this invention include methyl, ethyl, propyl, 1-methylethyl, butyl, 1-methylpropyl, 2-methylpropyl, and 1,1-dimethylethyl.

The term "alkoxyl" or "lower alkoxyl" means an alkyl group, as defined above, attached to the parent molecular moiety through an oxygen atom.

The term "halogen" contemplates fluorine, chlorine, or bromine.

Preferred compounds for the second component of the pharmaceutical compositions of this invention are those in which $R_1$, and $R_2$ are lower alkyl or lower alkoxyl. Particularly preferred for the second component of pharmaceutical compositions of this invention is the compound (Z)-N-(2,4,6-trimethoxyphenyl)-9-octadecenamide.

Particularly preferred as the first component of the pharmaceutical compositions of this invention is the compound 5-(2,5-dimethylphenoxy)-2,2-dimethylpentanoic acid (gemfibrozil).

Examples of preferred compounds for the second component of the pharmaceutical compositions of this invention are the following.

(Z)-N-(2,4,6-Trimethoxyphenyl)-9-octadecenamide.
(Z,Z)-N-(2,4,6-Trimethoxyphenyl)-9,12-octadecadienamide.
(Z,Z,Z)-N-(2,4,6-Trimethoxyphenyl)-9,12,15-octadecatrienamide.
(Z)-N-(2,4,6-Triethoxyphenyl)-9-octadecenamide.
(Z,Z)-N-(2,4,6-Triethoxyphenyl)-9,12-octadecadienamide.
(Z,Z,Z)-N-(2,4,6-Triethoxyphenyl)-9,12,15-octadecatrienamide.

The compound 5-(2,5-dimethylphenoxy)-2,2-dimethylpentanoic acid (gemfibrozil) and its method of preparation are disclosed in U.S. Pat. No. 3,674,836.

The compound 2-(4-chlorophenoxy)-2-methylpropanoic acid, ethyl ester (clofibrate) and its method of preparation are disclosed in U.S. Pat. No. 3,262,850.

The compound 2-[4-[2-[(4-chlorobenzoyl)amino]ethyl]phenoxy]-2-methylpropanoic acid (bezafibrate) and its method of preparation are disclosed in U.S. Pat. No. 3,781,327.

The compound 2-[4-(4-chlorobenzoyl)phenoxy]-2-methylpropanoic acid, 1-methylethyl ester (fenofibrate) and its method of preparation are disclosed in U.S. Pat. No. 3,907,792.

Gemfibrozil and bezafibrate may be used in the pharmaceutical compositions of this invention in their free acid form or in the form of a lower alkyl ester or a pharmaceutically acceptable metal or amine salt.

Esters are prepared by reacting the free acids with the desired lower alkyl alcohol in the presence of an ester condensation agent such as carbonyldiimidazole, dicyclohexylcarbodiimide and the like.

These acids also react to form pharmaceutically acceptable metal and amine salts. The term "pharmaceutically acceptable metal salt" contemplates salts formed with the sodium, potassium, calcium, magnesium, aluminum, iron, and zinc ions. The term "pharmaceutically acceptable amine salt" contemplates salts with ammonia and organic nitrogenous bases strong enough to form salts with carboxylic acids. Bases useful for the formation of pharmaceutically acceptable nontoxic base addition salts of compounds of the present invention form a class whose limits are readily understood by those skilled in the art. See, for example, S. M. Berge et al., *J. Pharm. Sci.*, 66: 1–19 (1977).

The free acid form of compounds of the present invention may be regenerated from the salt form, if desired, by contacting the salt with a dilute aqueous solution of an acid such as hydrochloric acid.

The base addition salts may differ from the free acid forms of the compounds of this invention in such physical characteristics as solubility and melting point, but are otherwise considered equivalent to the free acid form for the purposes of this invention.

The compounds of the present invention may exist in solvated or unsolvated form. In general, the solvated forms with pharmaceutically acceptable solvents such as water, ethanol and the like, are equivalent to the unsolvated forms for the purposes of this invention.

The first and second components of the pharmaceutical composition are present in a weight ratio of respectively between 1:1 and 1:3, preferably between about 1:2.

For preparing pharmaceutical compositions from the compounds of this invention, inert, pharmaceutically acceptable carriers can be either solid or liquid. Solid form preparations include powders, tablets, dispersable granules, capsules, and sachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about 5 to about 70% by weight of the active ingredient. Suitable carriers are magnesium carbonate, calcium stearate, magnesium stearate, talc, lactose, sugar, pectin, dextrin, starch, tragacanth, methyl cellulose, sodium carboxymethyl cellulose, and the like.

The term "preparation" is intended to include the formulation of the active compound with encapsulating material as a carrier providing a capsule in which the active component (with or without other carriers) is surrounded by a carrier, which is thus in association with it. In a similar manner, sachets are also included. Tablets, powders, sachets, and capsules can be used as solid dosage forms suitable for oral administration.

Liquid form preparations include solutions, suspensions and emulsions suitable for oral administration. Aqueous solutions for oral administration can be prepared by dissolving the active compound in water and adding suitable flavorants, coloring agents, stabilizers, and thickening agents as desired. Ethanol, propylene glycol and other pharmaceutically acceptable non-aqueous solvents may be added to improve solubility of the active components. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

In therapeutic use as hypolipidemic or hypocholesterolemic agents, the pharmaceutical compositions of this invention are administered to the patient at dosage levels of from 300 to 1200 mg per day of the lipid regulating agent, selected from gemfibrozil, clofibrate, bezafibrate, or fenofibrate, and from 600 to 2000 mg per day of the ACAT inhibiting agent in a combined formulation. For dosage forms which include up to 900 mg of gemfibrozil, the dosage may be in a single daily dose, preferably in a sustained-release formulation. When higher doses are prescribed, the daily dosage may be administered in two separate doses, administered twice daily.

The dosages, however, may be varied depending upon the requirements of the patient, the severity of the condition being treated, and the compound being employed. Determination of optimum dosages for a particular situation is within the skill of the physician.

The following examples illustrate particular methods for preparing the ACAT inhibitors and the pharmaceutical compositions of this invention. These examples are illustrative and are not to be read as necessarily limiting the scope of the invention as it is defined by the appended claims.

PREPARATION OF ACAT INHIBITORY COMPOUNDS

EXAMPLE 1

Preparation of (Z)-N-(2,4,6-Trimethoxyphenyl)-9-octadecenamide (Z)-9-Octadecenoyl chloride (oleic acid chloride, 75%, Aldrich Chemical Co., Milwaukee, Wisconsin, USA, 10.03 g, 0.025 mol) was dissolved in 75 ml of dry tetrahydrofuran. This solution was slowly added, with stirring, to a mixture of 4.7 g (0.025 mol) of 2,4,6- trimethoxyaniline (K & K Laboratories, 121 Express Street, Plainiview, New York, 11803 USA) and 2.52 g (0.025 mol) of triethylamine in 75 ml of dry tetrahydrofuran.

The resulting mixture was stirred at room temperature overnight, after which time the mixture was filtered and concentrated under vacuum. Water was added to the residue and the waxy material which formed was taken up in ethyl acetate. This organic solution was washed successively with portions of 1M aqueous hydrochloric acid, aqueous sodium bicarbonate solution, and saturated brine solution.

The organic solution was dried over anhydrous magnesium sulfate, the solvent evaporated, and the residue chromatographed on silica, eluting with 50:50 ethyl acetate:hexane (volume/volume) to yield 9.9 g of (Z)-N-(2,4,6-trimethoxyphenyl)-9-octadecanamide, mp 94°–95° C.

The infrared spectrum (KBr pellet) exhibited principal absorption peaks at 1649, 1609, and 1530 reciprocal centimeters.

Analysis for $C_{27}H_{45}NO_4$: Calculated: C, 72.44%; H, 10.13%, N, 3.13%; Found: C, 72.30%; H, 9.96%; N, 3.26%.

EXAMPLE 2

Preparation of (Z,Z)-N-(2,4,6-Trimethoxyphenyl)-9,12-octadecadienamide

Using the general method of example 1, but starting with 8.96 g (0.03 mol) of linoleoyl chloride, 5.5 g (0.03 mol) of 2,4,6-trimethoxyaniline, and 4.15 ml (0.03 mol) of triethylamine in 200 ml of tetrahydrofuran, there were prepared 9.2 g of (Z,Z)-N- (2,4,6-trimethoxyphenyl)-9,12-octadecadienamide, mp 87°–89° C.

Analysis for $C_{27}H_{43}NO_4$: Calculated: C, 72.77%; H, 9.73%, N, 3.14%; Found: C, 72.38%; H, 9.75%; N, 3.08%.

EXAMPLE 3

Preparation of (Z,Z,Z)-N-(2,4,6-Trimethoxyphenyl)-9,12,15-octadecatrienamide

Using the general method of Example 1, but starting with 8.9 g (0.03 mol) of linolenoyl chloride, 6.5 g (0.03 mol) of 2,4,6-trimethoxyaniline hydrochloride, and 8.3 ml (0.06 mol) of triethylamine in 200 ml of tetrahydrofuran, there were prepared 10.0 g of (Z,Z,Z)-N-(2,4,6-trimethoxyphenyl)-9,12,15-octadecatrienamide, mp 86°–88° C.

Analysis for $C_{27}H_{43}NO_4 \cdot 1/3 H_2O$: Calculated: C, 72.12%; H, 9.34%, N, 3.11%; Found: C, 72.14%; H, 9.44%; N, 3.11%.

PREPARATION OF PHARMACEUTICAL COMPOSITIONS

EXAMPLE 4

Capsule Formulation

To prepare 1000 No. 0 gelatine capsules, each containing 150 mg of lipid regulating agent and 300 mg of ACAT inhibitor, the following ingredients are employed.

Ingredients

| | | |
|---|---|---|
| 1. | Component A, lipid regulating agent selected from gemfibrozil, clofibrate, bezafibrate, and fenofibrate, 150 g. | |
| 2. | Component B, ACAT inhibitor, 300 g. | |
| 3. | Finely divided silicon dioxide, 15 g. | |
| 4. | Corn starch N.F., 141 g. | |
| 5. | Polysorbate 80 N.F., 4 g. | |
| 6. | Purified water, 80 ml. | |
| Method of Formulation | | |
| Step A: | Blend ingredients 1, 2, 3 and 4 in a suitable mixer. | |
| Step B: | Dissolve 5 in 6. | |
| Step C: | Granulate the blended ingredients of Step A with the ingredients of Step B in a suitable blender. | |
| Step D: | Dry the granulation at 40° C. overnight. | |
| Step E: | Mill the dried granulation of Step D using a Fitzmill No. 2RH screen with impact forward at high speed. | |
| Step F: | Fill No. 0 capsules with 610 mg each of the milled mixture from Step F. | |

EXAMPLE 5

Immediate-release Tablet Formulation

To prepare 1000 immediate-release tablets each containing 300 mg each of lipid regulating agent and 300 mg of ACAT inhibiting agent, the following ingredients are employed.

Ingredients

| | | |
|---|---|---|
| 1. | Component A, selected from gemfibrozil, clofibrate, bezafibrate, and fenofibrate, 300 g. | |
| 2. | Component B, ACAT inhibitor, 300 g. | |
| 3. | Finely divided silicon dioxide, 6 g. | |
| 4. | Pregelatinized starch 1551 N.F., 71 g. | |
| 5. | Hydroxypropylcellulose, 8 g. | |
| 6. | Polysorbate 80 N.F., 3 g. | |
| 7. | Purified water, 75 ml. | |
| 8. | Cellulose microcrystalline N.F., 33 g. | |
| 9. | Finely divided silicon dioxide, 5 g. | |
| 10. | Calcium stearate, 5 g. | |
| Method of Formulation | | |
| Step A: | Mill ingredients 1, 2, 3 and 5 through a No. 0 Screen. | |
| Step B: | B. Dissolve 6 in 7 and mix well. | |
| Step C: | Blend ingredients 1, 2, 3, 4, and 5, in a high intensity type mixer, using mixer and granulator modes for 3 minutes. | |
| Step D: | Granulate the mixture of ingredients from Step B together with the mixture from Step D. Add additional water if needed. | |
| Step E: | Spread the moist granulation from Step D on paper-lined trays and dry at 40° C. in a forced-air oven to an LOD of 2–3%. | |
| Step F: | Pass dried granulation from Step E, together with ingredients 8 and 9 through a Fitzmill No. 2RH screen, knives forward, medium speed. | |
| Step G: | Add ingredient 10 to the milled granulation from Step F and blend well. | |
| Step H: | Compress tablets on appropriate punches to a 10–12 Kp hardness. | |

EXAMPLE 6

Immediate-release Tablet Formulation

To prepare 1000 immediate-release tablets each containing 450 mg of lipid regulating agent and 450 mg of ACAT inhibitor, the procedure of Example 5 is followed utilizing the following ingredients.

Ingredients

| | | |
|---|---|---|
| 1. | Component A, selected from gemfibrozil, clofibrate, bezafibrate, and fenofibrate, 450 g. | |
| 2. | Component B, ACAT inhibitor, 450 g. | |
| 3. | Finely divided silicon dioxide, 9 g. | |
| 4. | Pregelatinized starch 1551 N.F., 106 g. | |
| 5. | Hydroxypropylcellulose, 5 g. | |
| 6. | Polysorbate 80 N.F., 12 g. | |
| 7. | Purified water, 100 ml. | |
| 8. | Cellulose microcrystalline N.F., 49 g. | |
| 9. | Finely divided silicon dioxide, 8 g. | |
| 10. | Calcium stearate, 8 g. | |

EXAMPLE 7

Immediate-release Tablet Formulation

To prepare 1000 immediate-release tablets each containing 450 mg of lipid regulating agent and 900 mg of ACAT inhibitor, the procedure of Example 6 is followed utilizing the following ingredients.

Ingredients

| | | |
|---|---|---|
| 1. | Component A, lipid regulating agent selected from gemfibrozil, clofibrate, bezafibrate, and fenofibrate, 450 g. | |
| 2. | Component B, ACAT inhibitor, 900 g. | |
| 3. | Finely divided silicon dioxide, 9 g. | |
| 4. | Pregelatinized starch 1551 N.F., 106 g. | |
| 5. | Hydroxypropylcellulose, 5 g. | |
| 6. | Polysorbate 80 N.F., 12 g. | |
| 7. | Purified water, 100 ml. | |
| 8. | Cellulose microcrystalline N.F., 49 g. | |
| 9. | Finely divided silicon dioxide, 8 g. | |
| 10. | Calcium stearate, 8 g. | |

EXAMPLE 8

Immediate-release Tablet Formulation

To prepare 1000 immediate-release tablets each containing 600 mg of lipid regulating agent and 600 mg of ACAT inhibitor, the procedure of Example 6 is followed utilizing the following ingredients.

Ingredients

| | | |
|---|---|---|
| 1. | Component A, lipid regulating agent selected from gemfibrozil, clofibrate, bezafibrate, and fenofibrate, 600 g. | |
| 2. | Component B, ACAT inhibitor, 600 g. | |
| 3. | Finely divided silicon dioxide, 12 g. | |
| 4. | Pregelatinized starch 1551 N.F., 141 g. | |
| 5. | Hydroxypropylcellulose, 16 g. | |
| 6. | Polysorbate 80 N.F., 6 g. | |
| 7. | Purified water, 150 ml. | |
| 8. | Cellulose microcrystalline N.F., 65 g. | |
| 9. | Finely divided silicon dioxide, 10 g. | |
| 10 | Calcium stearate, 10 g. | |

EXAMPLE 9

Immediate-release Tablet Formulation

To prepare 1000 immediate-release tablets each containing 300 mg of lipid regulating agent and 600 mg of ACAT inhibitor, the procedure of Example 6 is followed utilizing the following ingredients.

| | | |
|---|---|---|
| 1. | Component A, lipid regulating agent selected from gemfibrozil, clofibrate, bezafibrate, and fenofibrate, 300 g. | |
| 2. | Component B, ACAT inhibitor, 600 g. | |
| 3. | Finely divided silicon dioxide, 12 g. | |
| 4. | Pregelatinized starch 1551 N.F., 141 g. | |
| 5 | Hydroxypropylcellulose, 16 g. | |
| 6. | Polysorbate 80 N.F., 6 g. | |
| 7. | Purified water, 150 ml. | |
| 8. | Cellulose microcrystalline N.F., 65 g. | |
| 9. | Finely divided silicon dioxide, 10 g. | |
| 10. | Calcium stearate, 10 g. | |

Ingredients

EXAMPLE 10

Immediate-release Tablet Formulation

To prepare 1000 immediate-release tablets each containing 300 mg of lipid regulating agent and 900 mg of ACAT inhibitor, the procedure of Example 6 is followed utilizing the following ingredients.

Ingredients

| | | |
|---|---|---|
| 1. | Component A, lipid regulating agent selected from gemfibrozil, clofibrate, bezafibrate, and fenofibrate, 300 g. | |
| 2. | Component B, ACAT inhibitor, 900 g. | |
| 3. | Finely divided silicon dioxide, 12 g. | |
| 4. | Pregelatinized starch 1551 N.F., 141 g. | |
| 5. | Hydroxypropylcellulose, 16 g. | |
| 6. | Polysorbate 80 N.F., 7 g. | |
| 7. | Purified water, 150 ml. | |
| 8. | Cellulose microcrystalline N.F., 65 g. | |
| 9. | Finely divided silicon dioxide, 10 g. | |
| 10. | Calcium stearate, 10 g. | |

EXAMPLE 11

Sustained-release Tablet Formulation

To prepare 1000 sustained-release tablets each containing 450 mg of lipid regulating agent and 450 mg of ACAT inhibitor, the following ingredients are utilized.

Ingredients

| | | |
|---|---|---|
| 1. | Component A, lipid regulating agent selected from gemfibrozil, clofibrate, bezafibrate, and fenofibrate, 450 g. | |
| 2. | Component B, ACAT inhibitor, 450 g. | |
| 3 | Microcrystalline cellulose type CL611, 35 g. | |
| 4. | Cross carmellose sodium NF type A, 5 g. | |
| 5. | Eudragit E30D (Rohm & Haas), 180 g. | |
| 6. | Purified water, 35 ml. | |
| 7. | Talc USP, 5 g. | |
| 8. | Cross carmellose Na NF type A, 7 g. | |
| 9. | Ca stearate NF, 5 g. | |

Method of Formulation

| Step A: | Load ingredients 1, 2, 3 and 4 into a Collette Gral and mix for 3 minutes with the mixer at 200 rpm and the granulator speed set at 2. Add ingredient 5 while mixing and continue to mix for an additional 2 minute using the same mixing conditions. Use sufficient quantity of purified water to make the granulation. |
|---|---|
| Step B: | Spread the moist granulation on paper lined trays and dry in forced-air oven at 38-40° C. to an LOD of less than 1% |
| Step C: | Add ingredients 7 and 8. Pass the resulting mixture through a Fitzmill No. 2RH screen, knives forward at medium speed. |
| Step D: | Load the granulation into an appropriate blender and tumble blend for five minues. |
| Step E: | Withdraw a small portion of the granulation from the blender, add ingredient 9 through a No. 30 screen, mix well and return the mixture to the blender. Continue to tumble blend for an additional 5 minutes. |
| Step F: | Compress tablets at 10-12 Kp hardness using appropriate tooling. |

EXAMPLE 12

Sustained-release Tablet Formulation

To prepare 1000 sustained-release tablets each containing 600 mg of lipid regulating agent and 600 mg of ACAT inhibitor, the method of Example 11 was employed utilizing the following ingredients.

Ingredients

| | | |
|---|---|---|
| 1. | Component A, lipid regulating agent selected from gemfibrozil, clofibrate, bezafibrate, and fenofibrate, 600 g. | |
| 2. | Component B, ACAT inhibitor, 600 g. | |
| 3. | Microcrystalline cellulose type CL611, 46 g. | |
| 4. | Cross carmellose sodium NF type A, 7 g. | |
| 5. | Eudragit E30D (Rohm & Haas), 240 g. | |
| 6. | Purified water, 47 ml. | |
| 7. | Talc USP, 7 g. | |
| 8. | Cross carmellose Na NF type A, 75 g. | |
| 9. | Ca stearate NF, 7 g. | |

EXAMPLE 13

Sustained-release Tablet Formulation

To prepare 1000 sustained-release tablets each containing 300 mg of lipid regulating agent and 600 mg of ACAT inhibitor, the method of Example 11 was employed utilizing the following ingredients.

Ingredients

| | | |
|---|---|---|
| 1. | Component A, lipid regulating agent selected from gemfibrozil, clofibrate, bezafibrate, and fenofibrate, 300 g. | |
| 2. | Component B, ACAT inhibitor, 600 g. | |
| 3. | Microcrystalline cellulose type CL611, 46 g. | |
| 4. | Cross carmellose sodium NF type A, 7 g. | |
| 5. | Eudragit E30D (Rohm & Haas), 240 g. | |
| 6. | Purified water, 47 ml. | |
| 7. | Talc USP, 7 g. | |
| 8. | Cross carmellose Na NF type A, 75 g. | |
| 9. | Ca stearate NF, 7 g. | |

I claim:

1. A pharmaceutical composition comprising a lipid regulating effective amount of 5-(2,5-dimethylphenoxy)-2,2-dimethylpentanoic acid or a lower alkyl ester or pharmaceutically acceptable acid addition salt thereof, together with an ACAT inhibitory effective amount of (Z)-N-(2,4,6-trimethoxyphenyl)-9-octadecenamide, together with a pharmaceutically acceptable carrier; wherein the lipid regulating compound and the ACAT inhibitory compound are present in a weight ratio of 1:1.

2. A pharmaceutical composition comprising a lipid regulating effective amount of 2-[4-[2-[(4-chlorobenzoyl)amino]ethyl]phenoxy]-2-methylpropanoic acid) or a lower alkyl ester or pharmaceutically acceptable acid addition salt thereof together with an ACAT inhibitory effective amount of (Z)-N-(2,4,6-trimethoxyphenyl)-9-octadecenamide, together with a pharmaceutically acceptable carrier; wherein the lipid regulating compound and the ACAT inhibitory compound are present in a weight ratio of 1:1.

* * * * *